United States Patent [19]

Bokros

[11] 3,969,130

[45] July 13, 1976

[54] CARBON-COATED ARTICLES AND METHOD OF MAKING SAME

[75] Inventor: Jack C. Bokros, San Diego, Calif.

[73] Assignee: General Atomic Company, San Diego, Calif.

[22] Filed: Feb. 5, 1973

[21] Appl. No.: 329,526

[52] U.S. Cl. .................................. 117/332; 3/1.5; 428/334; 428/336; 428/368; 428/408; 427/2; 427/249; 428/448; 428/457
[51] Int. Cl. ..................... B44d 1/12; C01b 31/00
[58] Field of Search ........ 117/106 C, 106 A, 106 R, 117/216, 46 CG, 69, 226

[56] References Cited
UNITED STATES PATENTS

| | | | |
|---|---|---|---|
| 3,673,051 | 6/1972 | Clark et al. | 117/106 R X |
| 3,676,179 | 7/1972 | Bokros | 117/46 CG |
| 3,677,795 | 7/1972 | Bokros et al. | 117/106 C X |
| 3,684,585 | 8/1972 | Stroup et al. | 117/106 C X |
| 3,685,059 | 8/1972 | Bokros et al. | 117/46 C G X |

*Primary Examiner*—Ralph Husack
*Attorney, Agent, or Firm*—Fitch, Even, Tabin & Luedeka

[57] ABSTRACT

A pyrolytic carbon-coated article having improved wear resistance as a result of providing a thin wear-resistant layer just below the outer surface. The layer contains an alloy of pyrolytic carbon and a metal or metalloid carbide and is made by changing the composition in a deposition region without halting deposition so as to create transition regions adjacent the layer which include gradually lesser amounts of the alloying carbide.

10 Claims, No Drawings

CARBON-COATED ARTICLES AND METHOD OF MAKING SAME

The present invention relates to articles which are coated with pyrolytic carbon, and more particularly, it relates to methods of coating articles with pyrolytic carbon and to the resultant products of such methods.

It is already known to coat articles with pyrolytic carbon for a variety of purposes. Generally, the coating process is carried out by the deposition onto the surfaces of the articles of carbon that is formed by the high temperature decomposition (pyrolysis) of combination substances, such as volatile gaseous hydrocarbons. For example, U.S. Pat. No. 3,677,795, which issued on July 18, 1972 to Jack C. Bokros and Willard H. Ellis, teaches the making of prosthetic devices having coatings of pyrolytic carbon. U.S. Pat. No. 3,676,179, issued on July 11, 1972 to Jack C. Bokros, teaches the making of pyrolytic-coated articles having high strength characteristics by methods using the high temperature decomposition of a hydrocarbon or the like. A preferred method of coating disclosed in the foregoing patents involves the employment of a fluidized bed in which the hydrocarbon, or a mixture of the hydrocarbon with a carrier gas, is utilized to levitate the particle bed and the articles being coated.

It is an object of the present invention to provide pyrolytic carbon-coated articles having improved wear resistance. A further object is to provide improved pyrolytic carbon-coated articles that are designed to withstand concentrated wear. Another object is to provide an efficient and effective method for producing pyrolytic carbon-coated articles having improved wear resistance.

Generally, in accordance with the present invention, it is found that the wear resistance of a pyrolytic carbon-coated article is markedly improved if a thin layer or band is created near the outer surface which is made up of an alloy of pyrolytic carbon plus a substantial amount of a carbide additive which has good frictional wear characteristics. For example, the provision of a layer made up of an alloy containing a substantial amount of silicon carbide in a thickness as small as about 0.001 inch has been found to markedly increase the resistance to frictional wear. It is also important that there be some transition between the main pyrolytic carbon portion of the coating and the wear resistant layer so there is no interface appearing between the wear-resistant layer and the remainder of the coating that could have a detrimental effect on the strength of the composite article, as by causing the relatively thin layer to crack and/or become unbonded. Because pyrolytic carbon is disposed exterior of the wear-resistant layer, it reinforces the thin layer and presents an exterior surface that is primarily pyrolytic carbon and is thus more biocompatible.

It has been found that improved wear resistance is provided in a pyrolytic carbon-coated article by creating, in a region adjacent the surface thereof, a layer of an alloy having a high percentage of an additive carbide that exhibits such wear-resistant characteristics. To achieve this purpose, a metal or metalloid additive element is chosen which will form a carbide having such characteristics and which will alloy with the pyrolytic carbon. As pointed out in the aforementioned patents, it is known to alloy pyrolytic carbon coatings with such carbide-forming and alloying elements in relatively minor amounts in order to increase the overall structural strength of the resultant pyrolytic carbon coating. These additives may be similarly employed in such minor amounts throughout the main portion of the pyrolytic carbon coating in respect of the present invention. If it is desired to so alloy the main portion of the pyrolytic carbon coating, an additive will usually be chosen that is suitable for employment in a wear-resistant layer as well as for increasing structural strength generally. However, it is conceivable that a change in additive element could be effected when the wear-resistant layer is deposited.

Silicon is one example of an additive which may be so employed as it provides increased general structural strength when used in minor amounts and excellent wear resistance when provided in substantial proportions, and silicon is the preferred additive element. Examples of other carbide-forming elements which might be used as additives for increasing the structural strength of the main portion of the pyrolytic carbon coating include boron, hafnium, molybdenum, niobium, tantalum, titanium, tungsten, and zirconium. Such an additive element is generally used in an amount of about 10 to 15 weight percent to provide the desired increase in structural strength.

For the wear-resistant layer alone, silicon is also the preferred element; however, other carbide-forming metals and metalloids which produce a carbide exhibiting good resistance to frictional wear and which will alloy with carbon may also be used. Generally, elements from the foregoing group which provide carbides having good hardness may be used. To obtain the desired wear resistance, the additive is employed in an amount sufficient to provide an alloy which contains between 25 and about 80 volume percent of carbide, and preferably not more than about 50 volume percent. Optimum amounts may vary slightly depending upon the element chosen and even with regard to the ultimate use of the coated article; however, such amounts can readily be determined by empirical methods. For example, a wear-resistant layer may preferably contain silicon carbide in an amount between about 30 and about 40 volume percent.

It is considered that the thickness of such a wear-resistant layer should be at least about 0.001 inch. Although thicker layers can be employed, the use of a layer thicker than about 0.003 inch is not considered to be justified from the standpoint of improved wear-resistance. Usually a thickness greater than 0.01 inch would not be employed for this purpose; however, in some instances it may be advantageous to use the high carbide content wear-resistant material in depositing the entire portion of the coating interior of the exterior pyrolytic carbon layer. Redundancy in this coating may also be of some value, as it is in other structural applications. Accordingly, it may be desirable to provide a pair of spaced wear-resistant layers, each about 0.001 inch in thickness, separated by a layer of pyrolytic carbon containing a lesser amount of the alloying carbide, which separating layer might be between about 0.001 and about 0.01 inch in thickness and should be at least 0.0005 inch thick.

As previously indicated, it is desirable that an interface adjacent the wear-resistant layer be avoided inasmuch as the inclusion of such an interface might have an adverse effect on the overall strength and integrity of the coating. The amount of the additive element that is supplied to the depositon zone is preferably gradually increased, either from zero or from the minor amounts being used throughout the pyrolytic carbon coating, until the amount desired for the wear-resistant layer is reached. Operation in this manner assures that the desirable transition to the wear-resistant layer is provided. A similar gradual decrease preferably is employed upon the conclusion of deposition of the layer. It is believed that the regions adjacent the wear-resistant layer, for a distance of about 20 to 90 percent of the thickness of the layer, should contain amounts of the additive carbide to such an extent that the additive carbide is present in an average amount at least about 25 percent of the amount in which it is employed in the wear-resistant layer and preferably about 50 percent. These border regions should preferably be at least about 0.0005 inch thick. It is also possible to create the layer by increasing the amount of additive element to a peak and then similarly decreasing the composition so long as the result provides a central band at least about 0.001 inch thick having at least about 30 volume percent of carbide.

The articles which are provided with these improved pyrolytic carbon wear-resistant coatings may have any reasonable shape. However, the invention is of particular advantage with respect to articles which will be subjected to concentrated wear in particular locations. For example, they may be rods or cylinders that rotate or that are subject to relative motion axially thereof. Likewise, the invention is very effective in protecting complex shapes that will be subject to relative motion where the primary amount of wear will occur only in a few selected locations, as for example, in the case of a disc-type occluder for an artificial heart valve.

By the provision of a zone of pyrolytic carbon exterior of the wear-resistant layer, the article presents the outward appearance of a pyrolytic carbon-coated article which is important for biocompatibility. As earlier indicated, any distinct interface is avoided by gradually decreasing the amount of the additive element provided to the reaction zone while the region just exterior of the wear-resistant layer is being deposited. The overall article has the surface characteristics of a pyrolytic carbon-coated article whereas, in the region very close to the surface, preferably within about 0.003 inch thereof, although in some instances the distance may be 5 mils or more, there is provided this improved wear-resistant layer. Accordingly, although pyrolytic carbon itself exhibits good resistance to frictional wear, extended operation under concentrated wear conditions may cause the surface zone to be worn away in certain locations, in which instance, the wear-resistant layer will effectively halt further erosion in these regions of greatest frictional wear.

Accordingly, the invention provides a coating for an article to be protected which exhibits the desirable properties of pyrolytic carbon, either unalloyed or alloyed with slight amounts of a strength-improving carbide. However, disposed slightly below the exterior surface, there is provided a thin wear-resistant layer which substantially improves the performance of such an overall coated article in applications where it will be subject to repeated relative motion and therefore frictional wear. The effective life of the coated article in such applications is markedly extended.

Because it is the objective that the coated article exhibit good structural strength and wear-resistance, the pyrolytic carbon employed should complement this objective. The density of the pyrolytic carbon deposited should be at at least about 1.7 g/cm$^3$, and usually the density will be 1.8 g/cm$^3$ or greater. The overall thickness of the pyrolytic carbon coating should be thick enough to provide overall strength in a generally monolithic structure. The overall thickness of the coating will be at least about 0.006 inch, with the interior pyrolytic carbon layer being at least about 0.003 inch and for many applications, the thickness will be at least about 10 mils, with 15 mils often being an average thickness. Either laminar or isotropic carbon may be employed to produce coatings having good structural strength; however, isotropic carbon is preferred because it exhibits no tendency to delaminate and because stresses due to anisotropic expansion do not arise in isotropic coatings on irregular shapes at locations where small radii of curvature are encountered. Isotropic pyrolytic carbon having an apparent crystallite size of about 50A or less and which is deposited at temperatures of about 1500°C. and below is generally preferred.

The following Examples illustrate preferred processes for making wear-resistant articles coated with pyrolytic carbon and the preferred method of operation in a fluidized bed at a temperature at about 1500°C. or below. The pyrolytic carbon is deposited from a mixture of hydrocarbon and inert gas, and the additive element is conveniently provided in the deposition zone by bubbling the inert gas portion of the supply stream through a suitable reservoir containing the element as a part of a volatile compound. Operation in this manner provides a convenient way of changing the amount of the additive element being supplied by simply altering the amount of inert gas flow through the reservoir. The volatile compound can be injected directly into the mixed gas stream for it will be vaporized quickly at the temperatures in the deposition zone. A temperature at least above 1000°C. is contemplated. Although the illustrated processes employ propane as the hydrocarbon in the temperature range of about 1350° – 1400°C., it should be understood that other hydrocarbons can be employed and that higher temperatures may also be used. For example, methane may be employed at a temperature of 1800° to 2000°C. to deposit dense isotropic pyrolytic carbon.

EXAMPLE I

A wire strut approximately 0.03 inch in diameter is levitated in a vertical graphite reaction tube together with 100 grams of zirconium dioxide particles, having an average particle size of about 400 microns, which provide additional depositon surface area. The strut is made of an alloy of molybdenum and rhenium and is designed for use as a part of a heart valve which employs a disc occluder. The strut and particles are heated to a temperature of about 1350°C. while maintaining a flow of helium gas upward through the 3.5 inch diameter tube.

Propane gas is admixed with the helium to provide a total gas flow of about 18 liters per minute, having a partial pressure of propane of about 0.4 atmosphere (total pressure of 1 atmosphere). All of the helium is bubbled through a reservoir containing methyltrichlorosilane. The propane and the methyltrichlorosilane pyrolyze in the reaction zone and deposit onto the strut as isotropic carbon containing a minor amount of silicon carbide dispersed therein as an alloy. Deposition is continued until a coating about 7 mils (0.007 inch) thick is obtained, a time of about 30 minutes.

At this time, the deposition of the wear-resistant layer is ready to begin, and the propane flow is reduced to 3600 cc. per minute while the flow of helium is increased by 4000 cc. per minute, so the total flow is approximately 18.4 liters per minute, with all of the helium being bubbled through the methyltrichlorosilane. The change takes place over about 10 seconds. Because of mixing of the gas throughout the system and the deposition zone, the silicon carbide content being codeposited continuously increases to the maximum. Once this condition is reached, coating is continued for about 5 minutes, after which time a return to the original deposition conditions is effected by reversing the above-indicated procedure, and the coating is then continued for about 15 minutes. The coated strut is allowed to cool to about ambient temperature in a levitating flow of helium alone before being removed from the reaction tube.

Examination of the coated strut shows that the major portion of the coating is isotropic pyrolytic carbon having about 10 weight percent of silicon dispersed therein in the form of silicon carbide, as an alloy, and that the coating has a density of about 2 grams/cm$^3$. The pyrolytic carbon is the continuous phase of this alloy with the silicon carbide being present as the dispersed phase. The wear-resistant layer is about 0.002 inch in thickness with the zone bordering this layer where the transition in the composition of the deposition atmosphere took place, being about 0.0005 inch in thickness. The exterior pyrocarbon coating is about 3 to 4 mils thick.

Testing of a strut made by the process described above shows that it exhibits excellent resistance to frictional wear and that, in all other respects, the coated strut performs in essentially the same manner as a strut coated entirely with pyrolytic carbon of the type initially deposited thereon. Because of its shape, the wear on such an article is concentrated along a line near its base where it comes in contact with the disc occluder.

EXAMPLE II

A generally disc-shaped item made of graphite and designed to serve as an occluder in a heart valve, which has a major dimension of about 1 inch and a maximum thickness of about 0.15 inch, is introduced into the same reaction tube employed in Example I, together with a similar charge of 100 grams of zirconium oxide particles. The disc, particles and the reaction zone of the tube are heated to a temperature of about 1400°C. while a flow of helium gas is maintained therethrough to levitate the disc and particles.

Thereafter, propane is admixed with the helium to provide an atmosphere in the reaction zone having a partial pressure of propane of about 0.4 atmosphere (total pressure of one atmosphere). The total gas flow is maintained at about 20 liters per minute, and the propane undergoes pyrolysis and deposits isotropic pyrolytic carbon. Deposition is continued until an isotropic pyrolytic carbon coating about 10 mils thick is obtained, a time of about 40 minutes.

At this time, a gradually increasing portion of the helium flow is bubbled through a reservoir of methyltrichlorosilane, as in respect of Example I. After about a time period of 5 minutes, all of the 12 liters per minute flow of helium is passing through the methyltrichlorosilane. Thereafter, while maintaining the total flow at about 20 liters per minute, the flow of propane is decreased by 1000 cc. per minute every three minutes while the flow of helium is simultaneously proportionally increased until the flow constitutes 4000 cc. of propane and 16,000 cc. of helium per minute. This condition is maintained for about three minutes while a wear-resistant layer is deposited.

At the end of this time period, the foregoing steps are reversed until original conditions of 8 l./min. of propane and 12 l./min. of helium (without any bubbling through the methyltrichlorosilane) are achieved. The total time during which methyltrichlorosilane is introduced is about 31 minutes. Thereafter, coating is continued until an outer substantially pure pyrolytic carbon layer about 0.008 inch thick is deposited and deposition is halted. The article is cooled, removed and tested as in respect of Example I.

Examination shows that the pyrolytic carbon has a density of about 1.9 grams/cm$^3$, a BAF of about 1.1 and an apparent crystallite size of about 40A. The BAF is an accepted measure of preferred orientation of the layer planes in the carbon crystalline structure. The technique of measurement and a complete explanation of the scale of measurement is set forth in an article by G. E. Bacon entitled "A Method for Determining the Degree of Orientation of Graphite" which appeared in the Journal of Applied Chemistry, Volume 6, page 477 (1956). For purposes of explanation, it is noted that 1.0 (the lowest point on the Bacon scale) signifies perfectly isotropic carbon. The overall wear-resistant layer includes a band about 0.007 inch in thickness, wherein the centermost region contains about 30 volume percent silicon carbide and 70 volume percent carbon. The transition zones between the wear-resistant layer and the pure pyrolytic carbon coating regions each measure about 0.003 inch in thickness and show a gradual continuous increase (or decrease) in silicon carbide volume percentage.

Actual testing of the article under simulated use conditions shows that it exhibits excellent resistance to wear. In the regions where the maximum concentrated wear occurs, although the exterior pyrolytic carbon layer is very gradually worn away, the wear-resistant rich silicon carbide layer proves excellently wear-resistant and maintains its integrity.

Although the invention has been described particularly with regard to certain preferred embodiments, it should be understood that modifications and changes as would be obvious to one having the ordinary skill in the art may be made without departing from the scope of the invention which is defined in the appended claims.

Various of the features of the invention are defined in the claims which follow. What is claimed is:

1. A pyrolytic carbon-coated article having improved wear resistance, which article comprises a substrate of appropriate size and shape having an exterior coating of pyrolytic carbon, said pyrolytic carbon coating having a density of at least about 1.7 g./cm$^3$ and including a wear-resistant layer at least about 0.001 inch in thickness which contains carbon plus an additive carbide-forming element which is present in carbide form in said layer in an amount of at least 25 volume percent and not more than about 80 volume percent, said wear-resistant layer being located near the exterior surface of said coated article and providing excellent resistance to frictional wear.

2. An article in accordance with claim 1 wherein said pyrolytic carbon in a region bordering said wear-resistant layer includes said additive carbide in an average amount of at least about one-half of the percentage amount of carbide present in said wear-resistant layer.

3. An article in accordance with claim 2 wherein said wear-resistant layer is flanked by interior and exterior border regions which are each at least 0.0005 inch thick.

4. An article in accordance with claim 1 wherein said wear-resistant layer contains said carbide in an amount between about 30 and about 80 volume percent.

5. An article in accordance with claim 4 wherein said additive element is silicon.

6. An article in accordance with claim 5 wherein said wear-resistant layer contains silicon carbide in an amount between about 30 and 50 volume percent.

7. A method of making a pyrolytic carbon-coated article having improved wear resistance, which method comprises heating an appropriate substrate to a temperature about 1000°C. in a reaction zone, effecting deposition of pyrolytic carbon onto the surface of said heated substrate from an atmosphere containing a mixture of a hydrocarbon and an inert gas, after depositing at least about 0.003 inch of pyrolytic carbon, varying the composition of said mixture in said reaction zone without discontinuing deposition to provide a volatile compound containing a carbide-forming element in an amount sufficient to deposit an alloy of carbon and carbide, wherein said carbide constitutes between about 25 and about 80 volume percent, for time sufficient to deposit a wear-resistant layer, and then decreasing the amount of said volatile compound without discontinuing deposition so that the outermost portion of the coating contains no more than a minor amount of alloyed carbide.

8. A method in accordance with claim 7 wherein substantially all of said pyrolytic carbon is deposited from an atmosphere containing said carbide-forming element in an amount sufficient to codeposit at least a minor amount of carbide as an alloy therein.

9. A method in accordance with claim 8 wherein said carbide-forming element is provided by flowing said inert gas through a quantity of said volatile compound in liquid form and wherein said varying is effected by increasing the amount of inert gas flow through the liquid and decreasing the flow of the hydrocarbon.

10. A method in accordance with claim 7 wherein said varying to change said composition is accomplished over a time period of not less than about 10 seconds.

* * * * *

UNITED STATES PATENT AND TRADEMARK OFFICE
CERTIFICATE OF CORRECTION

PATENT NO. : 3,969,130

DATED : July 13, 1976

INVENTOR(S) : Jack C. Bokros

It is certified that error appears in the above-identified patent and that said Letters Patent are hereby corrected as shown below:

Column 3, line 37   "eariler" should be --earlier--.

Claim 7
Column 7, line 19   "about" should be --above--.

Signed and Sealed this

Thirtieth Day of November 1976

[SEAL]

Attest:

RUTH C. MASON
*Attesting Officer*

C. MARSHALL DANN
*Commissioner of Patents and Trademarks*